United States Patent [19]

Dane et al.

[11] Patent Number: 5,780,043

[45] Date of Patent: Jul. 14, 1998

[54] INFECTION RESISTANT THERMOPLASTIC POLYURETHANE

[76] Inventors: Greg Dane, Rue Clement Delpierre 44, 1310 La Hulpe; Jean Kersten, Chaussee de Tournai 259, 7931 Willers St Amand; Yves Delmotte, Rue de la Fontaine, 36, 7333 Tertre, all of Belgium

[21] Appl. No.: 544,915

[22] Filed: Oct. 18, 1995

Related U.S. Application Data

[63] Continuation of Ser. No. 175,939, Dec. 30, 1993, abandoned, which is a continuation of Ser. No. 842,012, Feb. 26, 1992, abandoned, which is a continuation-in-part of Ser. No. 795,695, Sep. 9, 1991, Pat. No. 5,181,276, which is a continuation of Ser. No. 484,137, Feb. 22, 1990, abandoned.

[51] Int. Cl.$^6$ ........................................ A01N 25/34
[52] U.S. Cl. .................. 424/404; 424/411; 424/78.17; 604/347; 604/346
[58] Field of Search ........................... 424/404, 405, 424/408, 409, 430, 486; 604/346, 347

[56] References Cited

U.S. PATENT DOCUMENTS

| | | | |
|---|---|---|---|
| 1,970,578 | 8/1934 | Schoeller et al. | 260/98 |
| 2,774,709 | 12/1956 | Mayhew et al. | 167/42 |
| 4,040,997 | 8/1977 | Van Vonno et al. | 260/23 XA |
| 4,393,871 | 7/1983 | Vorhauer et al. | 609/58 |
| 4,526,578 | 7/1985 | Wong | 604/892 |
| 4,544,694 | 10/1985 | Bower | 524/38 S |
| 4,581,028 | 4/1986 | Fox, Jr. et al. | 623/2 |
| 4,612,337 | 9/1986 | Fox, Jr. et al. | 623/2 |
| 4,612,340 | 9/1986 | Omachi | 524/296 |
| 5,019,096 | 5/1991 | Fox, Jr. et al. | 623/1 |
| 5,466,725 | 11/1995 | Kersten et al. | 523/122 |

OTHER PUBLICATIONS

Helanius A. and K. Simons, "Solubilization of Membranes by Detergents," Biochimica et Biophysica Acta, 415 (1975), pp. 29–79.

Byrdson, J.A. "Relation of Structure to Chemical Properties," Plastics Materials, Third Edition, pp. 83–89.

Chvapil, M., J.B. Ulreich, K. O'Dea, K. Betts, and W. Droegemueller, "Studies on Nonoxynol–9. III. Effect on Fibroblasts and Spermatozoa" Fertility and Sterility, vol. 33, No. 5, May 1980, pp. 521–525.

DeGroot–Kosolcharoen, J. and J.M. Jones, "Permeability of Latex and Vinyl Gloves to Water and Blood" Ameri. J. of Infect. Control, vol. 17, No. 4, (1989) pp. 196–201.

Greef, R.A., E.A. Setzkorn, and W.D. Leslie "A Colorimetric Method for the Determination of Parts/Million of Nonionic Surfactants" The J. of the Amer. Oil Chemists Society, vol. 42, Mar. 1965, pp. 180–185.

Griffin, W.C. "Classification of Surface–Active Agents by 'HLB'" J. of the Soc. of Cosmetic Chemists presented at the Oct. 11, 1949 meeting, pp. 311–326.

Paulssen, J., T. Eidem, and R. Kristiansen, "Perforations in Surgeons' Gloves," J. of Hospital Infection, (1988), 11, pp. 82–85.

Newspaper articles: published between Jun. 1991 and Feb. 1992 relating to Baxter's anti–AIDS glove (translated from French–including certificate of translation).

Baxter brochures in French, German and Dutch published Jun. 1991.

*Primary Examiner*—Neil S. Levy

[57] ABSTRACT

The present invention relates to infection resistant polyurethane having the infection resistant agents incorporated into the matrix of the thermoplastic polyurethane resin. This agent acts as a pool of infection resistant material. This infection resistant material can be used to make gloves and condoms.

4 Claims, 5 Drawing Sheets

INFECTION RESISTANT THERMOPLASTIC POLYURETHANE

RELATED APPLICATIONS

This application is a continuation of U.S. Ser. No. 08/175,939 filed Dec. 30, 1993, now abandoned, which is a continuation of U.S. Ser. No. 07/842,012 filed on Feb. 26, 1992, now abandoned, which is a continuation-in-part of U.S. Ser. No. 07/795,695, filed Sep. 9, 1991, now U.S. Pat. No. 5,181,276, which is a continuation of U.S. Ser. No. 07/484,137, filed Feb. 22, 1990, now abandoned.

BACKGROUND OF THE INVENTION

1. Field of the Invention

The present invention relates to infection resistant polyurethanes. More particularly, the invention relates to the incorporation of viricidal agents into a thermoplastic polyurethane matrix. These infection resistant polyurethanes can be used to make gloves, condoms and other items.

2. Description of the Prior Art

It is known that, for manufacturing devices from a molten blend of polymer, it is suitable to add same additives such as plasticizer(s) and antioxidant(s). It is also known to cover devices with a layer containing an antibacterial agent. For covering such devices, a composition containing a polymer, a solvent of said polymer and an antibacterial agent is prepared, said composition being then applied on the surface of the device so that, after drying, the device is provided with an antibacterial polymeric layer. Such devices are expensive and have antibacterial properties only on one surface thereof.

It is known to add to molten polyvinyl chloride benzoate of sodium or mercury salts for avoiding a microbial growth on said polymer; however, such additives are toxic for the health so that the use thereof has to be proscribed.

NONOXYNOL-9 (α-(nonylphenyl-w-hydroxypoly (oxy-1-2,ethanediyl), a nonionic surfactant has been described as an inhibitor of the growth of herpes simplex virus and HTLV-III. NONOXYNOL-9 (α-(nonylphenyl-w-hydroxypoly(oxy-1-2, ethanediyl), has also been used in spermicides. See Fox, U.S. Pat. No. 4,581,028.

SUMMARY OF THE INVENTION

This invention provides thermoplastic infection resistant polyurethane made by the process comprising: mixing a nonionic surfactant having a Hydrophilic Lipophilic Balance of between 12 and 20, the said compound consisting of:

where $R_1$ is a saturated or unsaturated hydrocarbon radical, $a_i$ is, for i=to n, an integer greater or equal to 2; $R_2$ is an organic radical, the constituent elements selected from the group consisting of carbon, hydrogen or oxygen, n is an integer selected so that the Hydrophilic Lipophilic Balance of said compound is between 12 and 20, said compound comprising at least 1% of thermoplastic polyurethane by weight, and a sufficient amount of an organic solvent to obtain a one phase solution and, combining this solution with thermoplastic polyurethane. Additionally, a plasticizer can be mixed with the nonionic surfactant.

The molten blend of this invention may thus, for example, be: extruded, injected or dip moulded so as to manufacture infection-resistant materials or devices; or sprayed on materials or devices so as to provide said materials or devices with a infection-resistant layer.

The invention also relates to infection resistant devices for example surgical gloves, surgical clothes, surgical operative fields, finger stalls, aprons, bibs, caps, condoms, etc. manufacturers for example by injecting into a mould a molten blend of a polymer mixed with the compound. The invention relates to composition of polymer(s) containing the compound, the compounds or/and compositions being suitable for the manufacture of viral infection-resistant devices according to the invention.

DETAILED DESCRIPTION OF THE INVENTION

Figure 1:
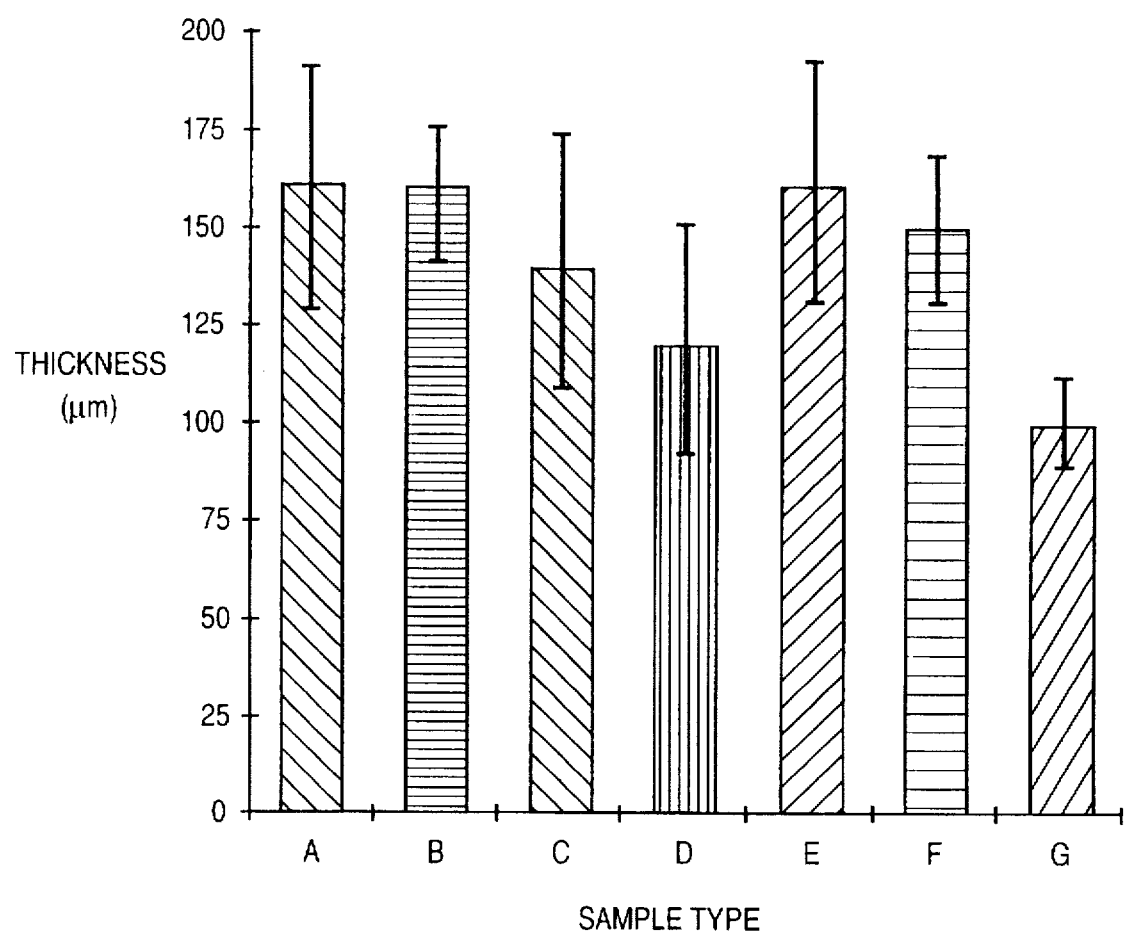
FIG. 1 shows thickness (μm) versus sample type.

Nonionic surfactants are compounds of the general formula:

where $R_1$ is a saturated or unsaturated hydrocarbon group;

$a_i$ is, for i=1 to n, an integer greater or equal to 2;

$R_2$ is an organic group possibly substituted, and n is an integer selected so that the Hydrophile-Lipophile Balance of said compound is comprised between 12 and 20.

Since the compounds of formula in which $R_1$, $R_2$, $a_i$ and n have the above given meanings does not affect the polymer network properties, such as tensile strength, elasticity modules, etc up to 10% or even more of said compounds may be added.

Compounds of general formula:

are known as being nonionic surfactants. These compounds may be characterized by a Hydrophile-Lipophile Balance as taught by GRIFFIN, W. C., J. Soc. Cosmet. Chem.1, 311–326 (1949). Such compounds are, for example, alkylphenoxypoly (ethyleneoxy) ethanol and more specifically ANTAROX (nonylphenoxypoly (ethyleneoxy) ethanol) ANTAROX 630 (nonylphenoxypoly(ethyleneoxy) ethanol), and NONOXYNOL-9 (α-(nonylphenyl-w-hydroxypoly (oxy-1-2, ethanediyl)). Methods for the manufacturing of such compounds are given for example, in U.S. Pat. Nos. 1,970,578 and 2,774,709.

It has been found that these compounds have viricidal action against Hepatitis B, C HIV-I and II, *Chlamydia trachomatis, Neisseria gonorhoerea, Trichomonas vaginalis, Candida albicans, Treponema pallidium,* and Herpes Simplex I & II. The compounds are stable at temperature of about 200° C.

Certain plasticizers can also be used to increase the incorporation of nonionic surfactant into a polymer and also to work as viscosity regulators of the solution. To act as a plasticizer, within the scope of this invention the plasticizer must have a molecular weight of at least 300. It should have a similar solubility parameter to that of the polymer. The solubility parameters can be determined by Small's method. Small, Relation of Structure to Chemical Properties, J. Appl.

Chem., 3:71 (1953). If the polymer has any tendency to crystallize it should be capable of some specific interaction with the polymer. It should not be crystalline solid at ambient temperature unless it is capable of specific interaction with the polymer. For example, from Table 5.6, of Small it can be seen that plasticizers for polyvinyl chloride such as the octyl phthalates, triolyl phosphate and dioctyl sebacate have solubility parameters within the 1 c.g.s unit of that the polymer.

On the other hand, dimethyl phthalate and the paraffinic oils which are not polyvinyl chloride plasticizers fall outside the range.

Most common acids used are:
ACETIC ACID
CITRIC ACID
ACONITIC ACID
TARTRIC ACID
ADIPIC ACID
SEBACIC ACID
TRIMELLITIC ACID
PHTHALIC ACID, etc.

The chain length of the alcohol molecules involved in the chemical reaction with a particular type of acid will give a compound which has to meet the requirements to act as a plasticizer.

Practically, phthalates prepared from alcohols with about eight carbon atoms are by far the most important class and probably constitute about 75% of the plasticizers used, more known as DEHP (Di ethyl Hexyl phthalate).

In the glove formulation, we use the di-iso nonyl phthalate (DINP), which formula is described here under.

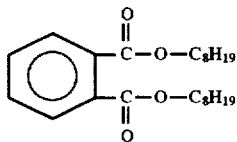

DINP: 1,2 BENZENEDICARBOXYLIC ACID, DI NONYL ESTER
PHTHALIC ACID, DINONYL ESTER
FORMULA: C26H4204

The thermoplastic polyurethane useful in this invention can be divided into categories: esters and ethers. More particularly, DESMOPAN KA 8500 (Bayer Co.) and DESMOPAN KU2-8600 (Bayer Co.) have been found to be useful. The selection of the thermoplastic polyurethane depends on the ultimate application of the material such as for a glove or condom.

In a method according to the invention, a nonionic surfactant and the plasticizer are solubilized in an organic solvent prior to adding to a polyurethane. When manufacturing for example disposable gloves, the compound of general formula will be distributed between the surface and the polymer matrix. For example, the plasticizer Di Iso Nonylphthalate and the nonionic surfactant NONOXYNOL-9 (α-(nonylphenyl-w-hydroxypoly (oxy-1-2,ethanediyl) are added to polyurethane pellets with the organic solvent such as tetrahydrofuran. Di Iso Nonylphthalate and NONOXYNOL-9 (α-(nonylphenyl-w-hydroxypoly (oxy-1-2,ethanediyl) are weighed in a glass beaker and then solubilized into a volume of solvent before being added to the polymer. The example section shows various amounts of nonionic surfactant and plasticizer in volumes of solvent. The specific amount selected is determined experimentally based on the surfactant, plasticizer and solvent selected and the end use of the infection resistant thermoplastic polyurethane.

Organic solvents that are useful in this invention include: tetrahydrofuran and 1,4 Dioxane. In general, any solvent with solubilization parameters close to those of the polymer will work. It should be noted, however, that solvents such as methyl ethyl ketone and ethyl acetate produce a swelling of the material without reaching complete solubilization. In these instances a combination of solvents may be an alternative to solve incomplete solubilization of the solvent with the polymer. The components are mixed to obtain a one phase solution of polyurethane and organic solvent.

Therefore, the infection-resistant devices according to the invention provide an viricidal properties including: contact protection and a protection mechanism in case of pinholes or microcracks.

Thus, in the case of a polymer based product the polymer network works as a reservoir for the nonionic surfactant, releasing on demand, an effective concentration of nonionic surfactant on both sides of the polymer film. This process provides two benefits: 1) by releasing nonionic detergent to the outside of the polymer film, surfactant that may have been removed by surface contact is replaced. Second, as surfactant is released to the inside, protection is provided from the many pinholes that developed in a thin polyurethane film.

EXAMPLE 1

Materials and Methods

Material:
Polyurethane RX 366: DESMOPAN KA 8550 (Bayer Co.) and RX 367: DESMOPAN KU2-8600 (Bayer Co.).

Methods:
Preparation of Solution

1) RX 366

Solution obtained by mixing 40 g of DESMOPAN KA 8550 (Bayer Co.) with 450 ml of tetrahydrofuran (8.9% weight/volume).

2) RX 366+10% NONOXYNOL-9 (α-(nonylphenyl-w-hydroxypoly (oxy-1-2,ethanediyl)

Same as for RX 366 but four g of NONOXYNOL-9 (α-(nonylphenyl-w-hydroxypoly (oxy-1-2,ethanediyl) are added to the polyurethane pellets before mixing with the 450 ml tetrahydrofuran. The 10% of NONOXYNOL-9 (α-(nonylphenyl-w-hydroxypoly (oxy-1-2,ethanediyl) is based on weight of thermoplastic polyurethane 3) RX 366+10% Di-Iso Nonylphtalate Same as for RX 366 but four g of Di-Isononylphtalate are added to the polyurethane pellets before mixing with 450 ml tetrahydrofuran.

4) RX 366+10% NONOXYNOL-9 (α-(nonylphenyl-w-hydroxypoly (oxy-1-2,ethanediyl)+5% Di-Isononylphtalate Same as for RX 366 but four g of NONOXYNOL-9 (α-(nonylphenyl-w-hydroxypoly (oxy-1-2,ethanediyl) and four g of Di-Isononylphtalate are added to the polyurethane pellets before mixing with 450 ml tetrahydrofuran.

5) RX 366+10% NONOXYNOL-9 (α-(nonylphenyl-w-hydroxypoly (oxy-1-2,ethanediyl)+10% di-iso nonylphtalate Same as for RX 366 by four g of NONOXYNOL-9 (α-(nonylphenyl-w-hydroxypoly (oxy-1-2,ethanediyl) and four g of di-iso nonylphtalate are added to the polyurethane pellets before mixing with 450 ml tetrahydrofuran.

6) RX 367+10% NONOXYNOL-9 (α-(nonylphenyl-w-hydroxypoly (oxy-1-2.ethanediyl)+5% Di-Iso Nonylphtalate Solution obtained by mixing forty g of DESMOPAN (Bayer Co.) KY2-8600 with four g NONOXYNOL-9 (α-(nonylphenyl-w-hydroxypoly (oxy-1-2.ethanediyl) and two g di-iso nonylphtalate before adding to 450 tetrahydrofuran.

Preparation of Films

The polymer solution is poured into a mold. The excess of material is removed using a mobile knife mounted on a support. The knife height is adjusted using micrometric screws. The coated molds were vaccum dried in an oven for one minute, powdered and stripped. Alternatively, any means used to remove excess organic solvent may be employed.

Mechanical Testing:

Technical conditions are summarized as follows:

The specimen were prepared according to ASTM D638M type M-II. Elongation, tensile at break and modulus are calculated on the graph obtained by the graph obtained by following certain dedicated test conditions:

grip separation: 25.4 mm (for thin sheating)

crosshead speed: 20% (200 mm/min)

load cell: 5N extension ratio i/10 mm: BE (strain conversion factor where 1 volt equals a strain of 49.2 mm).

These test can be conducted on standard material testing equipment such as a Zwick, and are routine for one skilled in the art of materials.

Thickness measurements are made based on ASTM D374, method C.

TABLE 1

| SAMPLE | THICKNESS (μM) | TENSILE (N/mm$^2$) | ELONGATION (%) | MODULUS (N/mm$^2$) |
|---|---|---|---|---|
| PVC glove | 160 + −30 | 11 + −1.7 | 290 + −47 | 7.9 + −0.69 |
| Viricidal PVC glove | 160 + −16 | 12 + −0.58 | 350 + −16 | 7.2 + −0.41 |
| RX366 | 140 + −34 | 36 + −3.3 | 570 + −37 | 8.6 + −1.2 |
| RX366 + N9 (10%) | 120 + −33 | 31 + −6.0 | 730 + −140 | 7.4 + −1.7 |
| RX366 + DINP (10%) | 160 + −26 | 37 + −4.7 | 640 + −46 | 7.6 + −0.98 |
| RX366 + N9 (10%) + DINP (5%) | 150 + −19 | 29 + −1.2 | 750 + −90 | 5.7 + −0.45 |
| RX367 + N9 (10%) + DINP (5%) | 100 + −13 | 29 + −4.4 | 550 + −130 | 6.6 + −0.66 |

EXAMPLE II

Each of the films prepared in Example 1 where tested for chemical extraction of nonionic surfactant. The method (Greff et Al: Determination of Nonionics. Journal of the American Oil Chemists' Society, Vol. 42 (1965), 180) is based on the formation of a blue complex between ammonium cobaltothiocyanate reagent and a polyethoxylated compound. The complex is extracted into benzene from a saturated salt solution and measured with a spectrophotometer at 320 μm. The absorbance reading is compared to a standard.

Materials and Reagents

Reagent

Ammonium thiocyanate

Cobalt nitrate hexahydrate 620 g of reagent grade ammonium thiocyanate and 280 g of reagent grade cobalt nitrate hexahydrate was dissolved in water and dilute to 1 liter. The reagent was extracted twice with benzene to obtain a blank reading.

Procedure 100 ml of sample solution was placed into a separatory funnel. 15 ml of ammonium cobaltothiocyanate reagent was added to 35–40 g of sodium chloride. The mixture was shaken to dissolve the salt and allowed to stand for 15 minutes. 25 ml of benzene was added to the funnel. The mixture was shaken for one minute, and then let stand to separate the layers. The lower aqueous layer was discarded and the organic layer was transfered to a centrifuge tube and spun for ten minutes. Using a spectrophotometer, the peak absorbance at 320 μm was read after scanning the region between 200 and 500μ against a reagent blank. The absorbance reading obtained on a sample was compared with a standard of know concentration.

Figure 5:
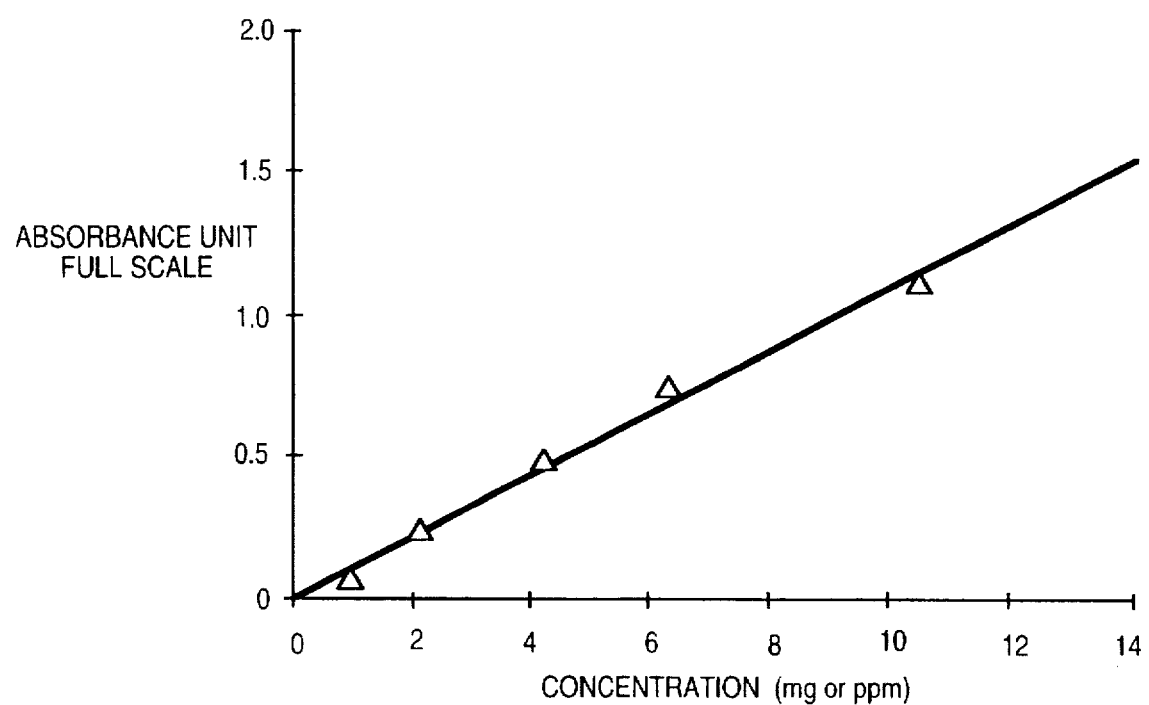
FIG. 5 shows a calibration curve for nonionic surfactant.

The data shown in FIG. 5 were obtained by testing various Antarox CO-630 (nonylphenoxypoly (ethyleneoxy) ethanol). The series was constituted of four samples containing respectively 2.1, 4.2, 6.3 and 10.5 mg of Antarox CO-630 (nonylphenoxypoly (ethyleneoxy) ethanol). The curve obtained is characterized by a correlation coefficient of 0.994.

Table 2 summarizes the data regarding the NONOXYNOL-9 (α-(nonylphenyl-w-hydroxypoly (oxy-1-2.ethanediyl) (α-(nonylphenyl-w-hydroxypoly (oxy-1-2, ethanediyl) extraction from the thermoplastic polyurethane film made in Example 1.

TABLE 2

| POLYURETHANE FILM | N9 CONCENTRATION (*) |
|---|---|
| Film 1 | |
| RX366 + DINP (10%) | 0 mg |
| RX366 + DINP (10%) | 0 mg |
| Film 2 | |
| RX366 + N9 (10%) | 11.34 mg |
| RX366 + N9 (10%) | 10.53 mg |
| Film 3 | |
| RX366 + N9 (10%) + DINP (5%) | 11.88 mg |
| RX366 + N9 (10%) + DINP (5%) | 11.52 mg |

* Results obtained from the extraction of 108 square cm. of each film in 900 ml of water for 30 min.

This data shows that for film 2 NONOXYNOL-9 (α-(nonylphenyl-w-hydroxypoly (oxy-1-2.ethanediyl) is present in the films. The results performed on the third type of film show that in the presence of 5% Di Iso Nonylphthalate, the amount of extracted NONOXYNOL-9 (α-(nonylphenyl-w-hydroxypoly (oxy-1-2.ethanediyl) is the same.

EXAMPLE III

Mechanical Properties

Samples A and B are gloves made of polyvinyl chloride. Samples C, D, E, F and G are polyurethane films of varying thickness.

TABLE 3

Analysis of Thermopolyurethanes

Sample Type
A: Polyvinylchloride (glove)
B: Polyvinylchloride containing 10% NONOXYNOL-9
C: Desmopan KA8550 (Bayer Co.) (polyurethane)
D: Desmopan KA8550 (Bayer Co.) containing 10% NONOXYNOL-9
E: Desmopan KA8550 (Bayer Co.) containing 10% DINP
F: Desmopan KA8550 (Bayer Co.) containing 10% NONOXYNOL-9 and 5% DINP
G: Desmopan KU2-8600 (Bayer Co.) containing 10% NONOXYNOL-9 and 5% DINP Sample A: Polyvinylchloride made of plastisol as described page 12 of U.S. Ser. No. 484,137; Sample B: Polyvinylchloride containing 10% NONOXYNOL-9 (α-(nonylphenyl-w-hydroxypoly (oxy-1-2, ethanediyl); Sample C: RX366 DESMOPAN KA8550 (Bayer Co.); Sample D: RX366 containing 10% NONOXYNOL-9 (α-(nonylphenyl-w-hydroxypoly (oxy-1-2, ethanediyl);

Sample E: RX366 containing 10% Di Iso Nonylphthalate;

Sample F: RX366 containing 10% NONOXYNOL-9 (α-(nonylphenyl-w-hydroxypoly (oxy-1-2,ethanediyl) and 5% Di Iso Nonylphthalate;

Sample G: RX367 DESMOPAN KU2-8600 (Bayer Co.) containing 10% NONOXYNOL-9 (α-(nonylphenyl-w-hydroxypoly (oxy-1-2,ethanediyl) and 5% Di Iso Nonylphthalate.

Thickness

When the viscosity of the polymer solution containing NONOXYNOL-9 (α-(nonylphenyl-w-hydroxypoly (oxy-1-2,ethanediyl) is lowered, the thickness of the polyurethane film is decreased. In fact, NONOXYNOL-9 (α-(nonylphenyl-w-hydroxypoly (oxy-1-2,ethanediyl) added to the polymer solution decreases the viscosity which induces a decrease of the film thickness. (FIG. 1. Sample type D) This is observed by comparing respectively D and C as well as F and E. G is another sample made of another type of polyurethane. See FIG. 1.

Elongation and Modulus

Figure 2:
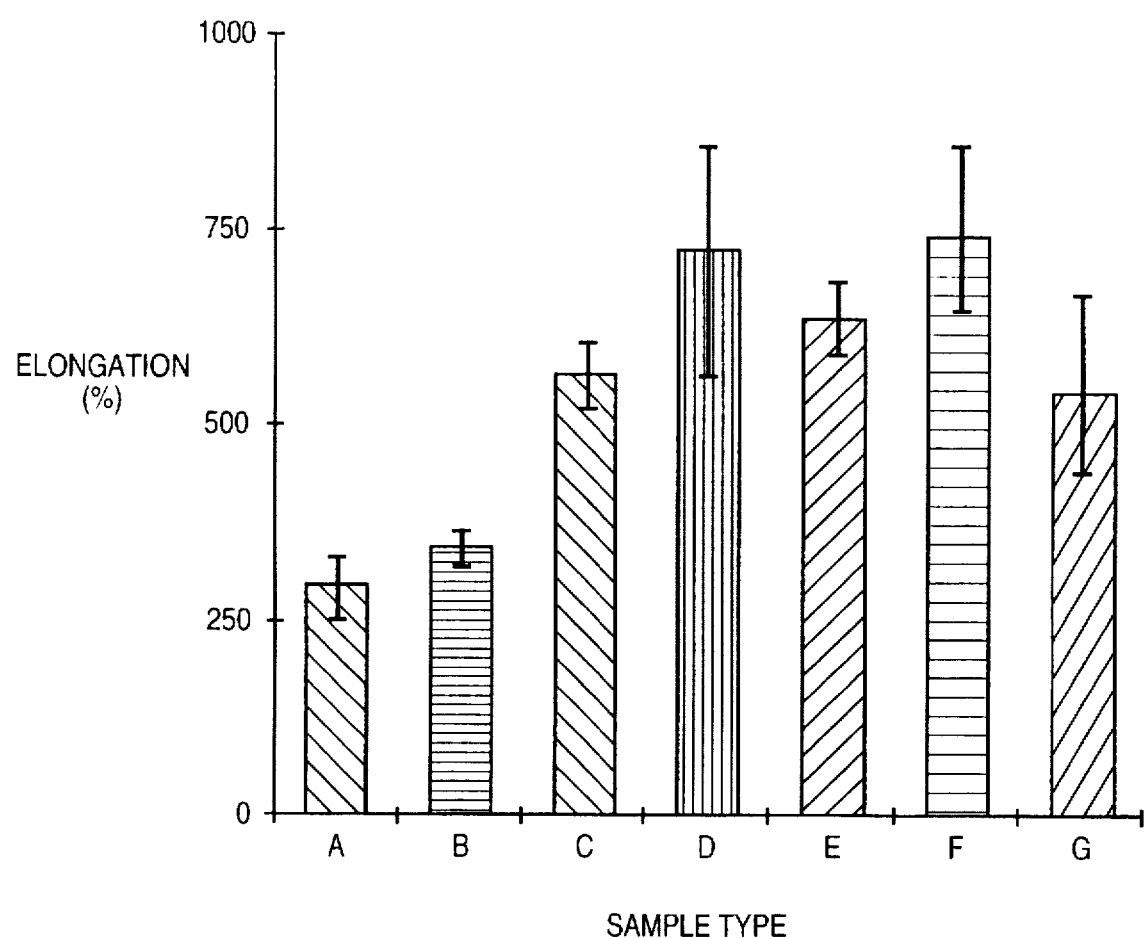
FIG. 2 shows percent elongation versus sample type.
Figure 4:
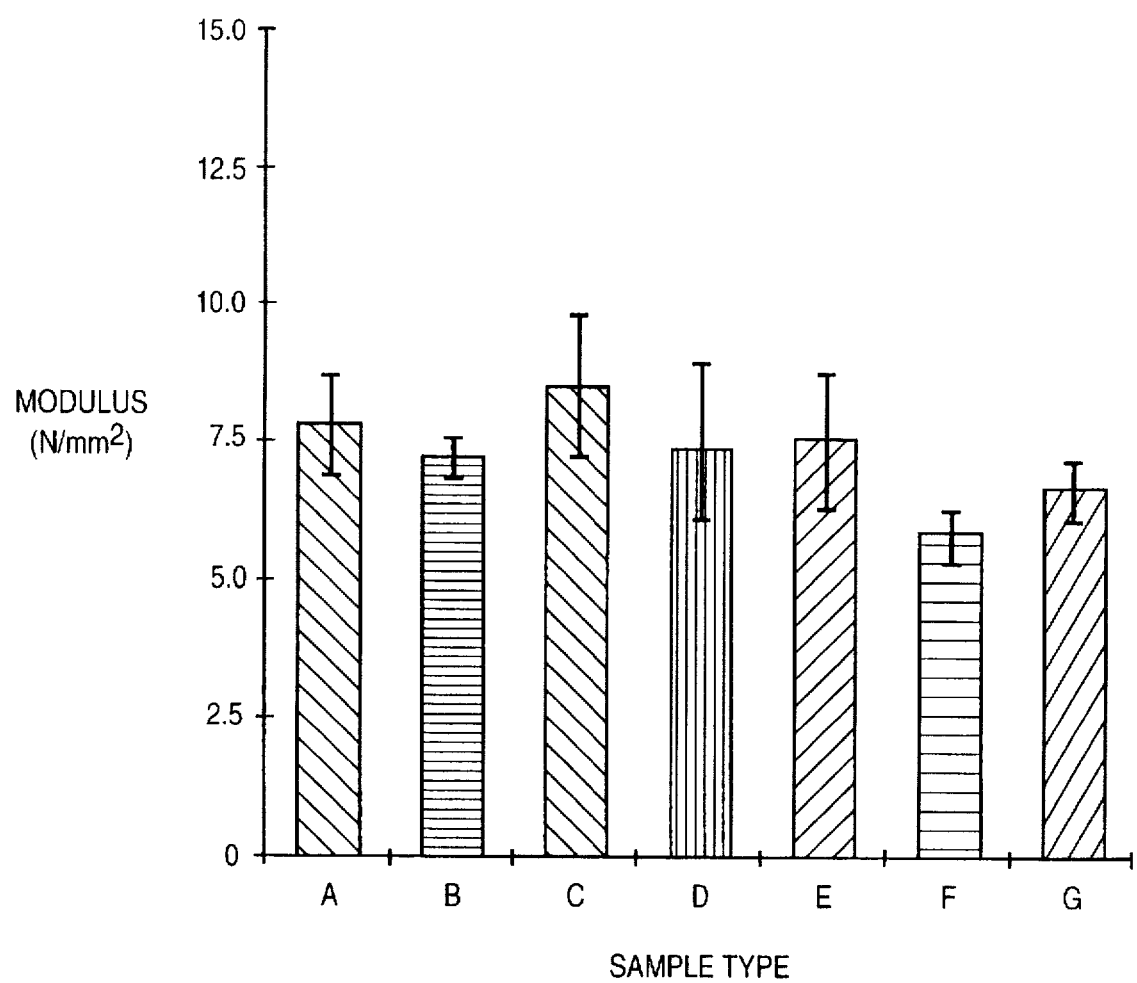
FIG. 4 shows modules (N/mm²) versus sample type.

NONOXYNOL-9 (α-(nonylphenyl-w-hydroxypoly (oxy-1-2,ethanediyl), incorporated into the thermoplastic polyurethane, increases the elongation and decreased the modulus. See FIGS. 2 and 4.

As expected, the plasticizing effect of the NONOXYNOL-9 (α-(nonylphenyl-w-hydroxypoly (oxy-1-2,ethanediyl) slightly decreases the modulus but increases the elongation property. The incorporation of 5% di-iso nonylphtalate into the DESMOPAN KA 8550 (Bayer Co.) containing 10% NONOXYNOL-9 (α-(nonylphenyl-w-hydroxypoly (oxy-1-2,ethanediyl) allows to control the viscosity of the polymer solution. Tensile at break, elongation and modulus are in the same range than the 10% NONOXYNOL-9 (α-(nonylphenyl-w-hydroxypoly (oxy-1-2,ethanediyl) formulation. Films made of Rx366 with 10% NONOXYNOL-9 (α-(nonylphenyl-w-hydroxypoly (oxy-1-2,ethanediyl) and 10% di-iso nonylphtalate had elongation values out of the range of the test system.

Tensile at break

Figure 3:
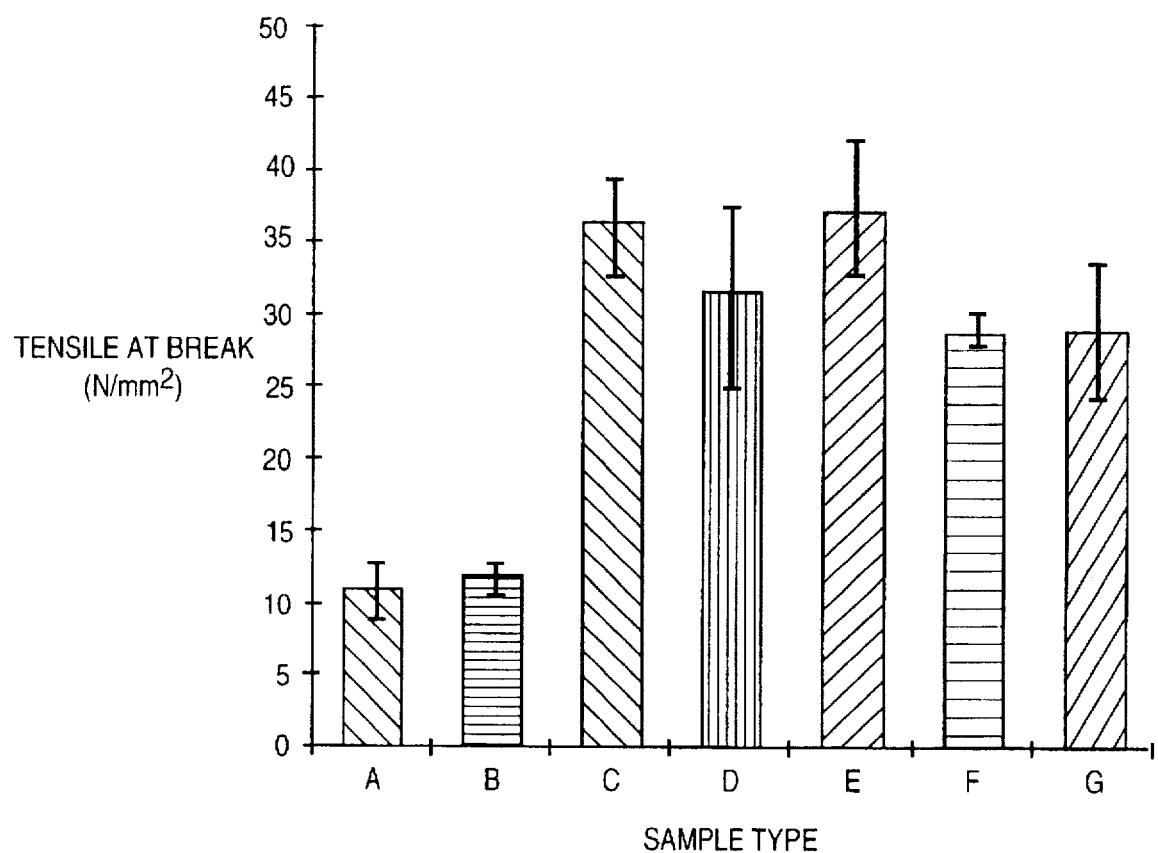
FIG. 3 shows tensile at breaks (N/mm²) versus sample type.

A concentration of 10% NONOXYNOL-9 (α-(nonylphenyl-w-hydroxypoly (oxy-1-2,ethanediyl) in DESMOPAN KA 8550 (Bayer Co.) slightly decreases the tensile at break of the thermoplastic polyurethane. Here two polyvinyl chloride samples are differentiated from the polyurethane samples which have "tensile at break" value three times higher. Samples D and F have "tensile at break" values decreasing slightling when compared to sample C. Sample E value is comparable to sample C. See FIG. 3.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. An infection resistant thermoplastic polyurethane device selected from the group consisting of: gloves, condoms, surgical clothes, finger stalls, aprons, bibs, caps and surgical operative fields formed by the process consisting essentially of:

a) mixing a non-ionic surfactant with a thermoplastic polyurethane polymer and a plasticizer having a molecular weight greater than 300, to form a mixture, the non-ionic surfactant having the formula:

$R_1-O-((CH_2)a_i-O)n-R_2$ wherein $R_1$ is a saturated or unsaturated hydrocarbon radical; $a_i$ is for I=n, an integer greater or equal to 2; $R_2$ is an organic radical selected from the group consisting of C—H and C—O and n is an integer selected so that the Hydrophilic Lipophilic Balance of the surfactant is between 12 and 20;

b) combining the mixture with a sufficient amount of an organic solvent selected from the group consisting of tetrahydrofuran and 1,4 dioxane to form a one-phase solution; and c) forming the thermoplastic polyurethane device.

2. The infection resistant device of claim 1 wherein the surfactant comprises at least 1% of the polymer by weight.

3. The infection resistant device of claim 1 wherein the non-ionic surfactant is (α-(nonylphenyl)-w-hydroxypoly (oxy-1,1 ethanediyl 1)).

4. The infection resistant device of claim 1 wherein the plasticizer is di-isononylphthalate.

* * * * *